(12) United States Patent
Jordan et al.

(10) Patent No.: US 7,063,233 B2
(45) Date of Patent: Jun. 20, 2006

(54) METHOD OF FOLDING GLOVES AND DISPENSER THEREFOR

(75) Inventors: Earl Jordan, Aliso Viejo, CA (US); Paul R. Persiani, Aliso Viejo, CA (US)

(73) Assignee: Oneglove, LLC, Laguna Woods, CA (US)

( * ) Notice: Subject to any disclaimer, the term of this patent is extended or adjusted under 35 U.S.C. 154(b) by 110 days.

(21) Appl. No.: 10/172,192

(22) Filed: Jun. 13, 2002

(65) Prior Publication Data

US 2003/0230591 A1 Dec. 18, 2003

(51) Int. Cl.
*B65H 1/00* (2006.01)
*B65H 1/08* (2006.01)
*A47K 10/24* (2006.01)

(52) U.S. Cl. .................. 221/197; 221/48; 221/49; 221/52; 221/198; 221/46; 221/58; 221/63

(58) Field of Classification Search ............. 221/48, 221/49, 52, 58, 61, 63, 197, 198, 46
See application file for complete search history.

(56) References Cited

U.S. PATENT DOCUMENTS

| | | | |
|---|---|---|---|
| 4,863,084 A | 9/1989 | Nabozny | |
| 4,896,773 A | 1/1990 | Zilio | |
| 4,951,815 A | 8/1990 | Ulbrich | |
| 4,993,589 A * | 2/1991 | McLaughlin | 221/33 |
| 4,997,105 A | 3/1991 | Fischer | |
| 5,044,493 A | 9/1991 | Crawford et al. | |
| 5,044,494 A | 9/1991 | Tamura | |
| 5,088,620 A * | 2/1992 | Kelliher et al. | 221/59 |
| 5,096,089 A | 3/1992 | McLaughlin | |
| 5,175,977 A * | 1/1993 | Crawford et al. | 53/399 |
| 5,265,785 A | 11/1993 | Chudy | |
| 5,392,974 A | 2/1995 | Johnson-Rabbett | |
| 5,740,943 A | 4/1998 | Shields et al. | |
| 5,816,440 A | 10/1998 | Shields et al. | |
| 5,896,983 A | 4/1999 | Wood | |
| 6,021,919 A * | 2/2000 | Kelly | 221/25 |
| 6,708,841 B1 * | 3/2004 | Baughman | 221/46 |

* cited by examiner

*Primary Examiner*—Gene O. Crawford
*Assistant Examiner*—Michael E Butler
(74) *Attorney, Agent, or Firm*—Christie, Parker & Hale, LLP.

(57) ABSTRACT

A method of interfolding gloves including superposing finger portion of second glove adjacent finger portion of first glove, with second glove finger portion being disposed parallel and in a direction opposite the first glove finger portion, in a superjacent opposing relationship. First glove hand and cuff are lapped over second glove finger, to create lapped, superjacent opposing fold. By repeatedly lapping previous glove hand over subsequent glove fingers, a glove bundle is formed. Folding can be longitudinal before lapped, superjacent opposing folding. Gloves are disposed in portable dispenser with lapped, superjacent folding and dispensing opening cooperating to dispense one glove, cuff first.

22 Claims, 10 Drawing Sheets

METHOD OF FOLDING GLOVES AND DISPENSER THEREFOR

BACKGROUND OF THE INVENTION

1. Field of the Invention

The present invention relates to disposable gloves and dispensers therefor, and in particular a method of folding disposable gloves, and a dispenser adapted to dispense the disposable gloves.

2. Description of Related Art

An unremitting upsurge in disposable glove use continues for over two decades. The initial surge occurred in 1985, when The Centers for Disease Control and Prevention (CDC) developed the strategy of "universal blood and body fluid precautions," which are based on the premise that all patients should be assumed to be infectious for HIV and other bloodborne pathogens. These strategies were formalized in "CDC Guidelines for Prevention of Transmission of Human Immunodeficiency Virus and Hepatitis B Virus to Health-Care and Public-Safety Workers," MMWR 1989; 38(S-6):1–36. In general, "universal precautions" requiring disposable glove use should be followed when workers are exposed to blood, certain other body fluids (amniotic fluid, pericardial fluid, peritoneal fluid, pleural fluid, synovial fluid, cerebrospinal fluid, semen, and vaginal secretions), or any body fluid visibly contaminated with blood. In recent years, many antibiotic-resistant, virulent, and lethal microorganisms have become increasingly widespread, including human immunodeficiency virus (HIV), hepatitis B, necrotizing *staphlococcus,* Vancomycin-resistant enterococcus and multidrug-resistant tuberculosis. The use of gloves as a barrier to prevent transmission of microorganisms between patients and health care professionals has become a predominant issue in today's clinical settings, including physicians' and dentists' offices.

Disposable glove use is burgeoning beyond the clinical setting, as well. Emergency, law enforcement, correctional facility, and public-safety workers often encounter unpredictable and emergent exposures, which may make the identification of hazardous body fluids very difficult and often impossible. Furthermore, not only must workers be protected from exposure to blood and other potentially infectious body fluids in the course of their work activities, they also must protect others from infection through cross-contamination. For example, childcare and preschool centers, and even kindergartens, have become transmission points for antibiotic-resistant blood-borne pathogens.

Many workers in diverse occupations such as, in the electronics, medical device, pharmaceutical, agricultural, nuclear, industrial chemical and pesticide handling, waste management, painting, cosmetic, and body art industries and services increasingly look to a ready supply of disposable gloves to reduce their exposure to, and skin contact with, potentially hazardous materials. These materials can include toxic chemicals, pesticides, cytotoxic drugs, radioactive materials, and human, animal, or biological tissues, fluids, and wastes. Moreover, increased public concerns regarding the transmission of disease have led to measures to protect food during preparation and service.

Thus, disposable gloves have become the most ubiquitous form of barrier-type personal protective equipment, creating a $3 billion latex and synthetic glove market in 2001, in which nearly 27 billion gloves were sold in the USA alone. In many settings, disposable gloves are either legally mandated or considered to be integral with the principles of good practice.

Disposable gloves should fit properly, and should not be washed or reused. Also, gloves should be replaced once soiled or damaged, and in-between patients, victims, products, and work areas. It is desirable that even non-sterile disposable gloves be kept as clean as possible prior to use. Otherwise, biological and physical contaminants may be inadvertently transferred to the patient, the product, or the work area by the soiled gloves. Accordingly, it is most desirable to minimize contact with the finger portions of clean gloves.

Typically, disposable gloves are dispensed in random orientations from large containers or open plastic bins located at stationary points, which are subject to gross manipulation. These containers usually hold 100 or more gloves, are fixed to a sink, wall, or bulkhead, and may be covered by a metal, plastic, or wooden cover, primarily for cosmetic purposes. Often, these covers themselves can become reservoirs for pathogens. Also, these dispensers can be at some distance from the patients or work areas. If a worker exhausts their immediate supply of gloves, another trip to the dispenser site is required. As a result, glove users are often compelled to haphazardly cram extra gloves into pockets, pouches, and sacks, a practice which can grossly soil clean gloves, can intermingle clean objects with contaminated objects, and can lead to gloves falling out of pockets at inopportune moments.

Existing portable disposable glove holders do allow glove users to carry a ready supply of gloves. However, these portable disposable glove holders are reusable and refillable. With each subsequent reuse comes an additional risk of cross-contamination of the container, and thus the gloves, with accumulated microbes, chemical agents, dust, soil, blood, and any other particulate foreign material. Furthermore, such portable dispensers are refilled by manually cramming a quantity of randomly-oriented gloves, which first were plucked from a dispenser, such that gloves are handled by contact with whatever glove surface may be present at the dispenser opening, including the fingers.

For example, in U.S. Pat. No. 5,392,974, issued to Johnson-Rabbett on Feb. 28, 1995, and entitled "Medical glove holder," a glove holder is disclosed that is adapted to be carried by the belt of the user, particularly, emergency medical personnel, and that is adapted for use with a substantial supply of protective gloves. Also, a dispensing opening, intended to dispense one glove at a time, is provided. This glove holder, however, is a reusable pouch made from flexible sheet material sewn together to form gusset-fold sides and a closure flap on top. The dispensing opening is a restrictive slit in front side of the sheet material that constrains the movement of gloves "stuffed" in random orientation therein. The reuse of the pouch and manipulation of the gloves during loading and unloading can encourage gross contamination of the dispenser and otherwise clean gloves. Furthermore, even if treated, fabric can attract and harbor pathogens.

As another example, in U.S. Pat. No. 5,265,785, issued to Chudy on Nov. 30, 1993, and entitled "Protective glove provider," a portable canister includes removably, lockably, interconnected body and base members which are comprised of semi-rigid materials, and are configured to provide a rigid canister when the members are joined. The body, which can be cylindrical, has an end wall of reduced thickness, relative to the rest of the body. In the thinner end wall is an aperture defined by flexible spokes through which gloves can be inserted and removed. The base member is provided to provide structural rigidity to the body member, and to attach thereto means for attaching the canister to a glove user or a convenient object.

As before, the glove holder is reusable, and replacement gloves are randomly stuffed into the canister, potentially leading to gross contamination of the gloves and accumulation of particulate foreign material on the canister. In addition, the canister is generally cylindrical, and can intrude against the waist of the user. This may lead to discomfort in situations where glove users are required to crouch and bend while rendering assistance or performing their duties.

SUMMARY OF THE INVENTION

The present invention meets the aforementioned needs by providing a method of interfolding gloves. Each glove has a finger portion, a hand portion, and a cuff portion. The method includes superposing the finger portion of a second glove approximately adjacent the fingers of the first glove, with the second glove finger portion being disposed approximately parallel and oriented in a direction generally opposite the first glove finger portion. Thus, the second glove finger portion is in a superjacent opposing relationship relative to the first glove finger portion. The method also includes the operation of lapping the hand portion and the cuff portion of the first glove over the finger portion of the second glove, such that at least one lapped, superjacent opposing fold is provided thereby.

In addition, the method can further include repeatedly superposing the finger portion of a subsequent glove of a plurality of gloves approximately adjacent the fingers of a previous glove of a plurality of gloves, and repeatedly lapping the hand portion and the cuff portion of the previous glove over the finger portion of the subsequent glove, such that a lapped, superjacent opposing fold is provided thereby. The subsequent glove finger portion is disposed approximately parallel and oriented in a direction generally opposite the previous glove finger portion. As before, the subsequent glove finger portion is in a superjacent opposing relationship relative to the previous glove finger portion. After a predetermined number of gloves have been thus folded, a glove bundle is formed. In one aspect of the invention, the cuff portion and at least some of the hand portion of the last glove thus folded lie near the top of the glove bundle, in a generally cuff-first orientation, although a finger-first orientation may be preferred in certain embodiments. The glove bundle then can be encased in a container configured to hold the glove bundle.

In another embodiment of the present invention, each of the previous and subsequent gloves is approximately transversely folded along a respective longitudinal axis prior to forming a superjacent-opposing fold. The transverse fold can be a bifold, trifold, a partial fold, a tuck, a pleat, a crimp, or a combination thereof.

In another embodiment of the invention, the method includes disposing the glove bundle in a glove dispenser, each adjacent glove in the glove bundle exerting an attractive force upon another adjacent glove in the glove bundle, the glove dispenser including a dispensing opening adapted to provide a counterforce in cooperation with the attractive force to dispense a preselected number of gloves at a time, such as one glove being dispensed at a time through the dispensing opening, with the glove bundle being arranged to dispense the glove through the dispensing opening in a cuff-first orientation.

The invention also provides an embodiment having a glove dispenser adapted to contain a glove bundle having a predetermined number of gloves folded in a lapped, superjacent-opposing fold format. The dispenser includes a case; a cap enclosing the case and having a dispensing opening therethrough; and an attachment device coupled to the case. The dispensing opening is adapted to cooperate with a tension of the glove bundle to dispense one glove at a time in a cuff-first orientation. The tension can be an attractive force, such as a frictional or stictional force, between adjacent folded gloves in the glove bundle. Also, in one aspect of the glove dispenser, the cap is fixed to the case after the glove bundle has been disposed therein. In still another aspect of the glove dispenser, the cap is sealably fixed to the case after the glove bundle has been disposed therein. In yet another aspect of the invention, at least one of the cap and the case is a structure composed of suitable natural, synthetic, composite, and laminate materials, including, without limitation, paper and board materials; foils; and plastics such as polypropylene; polyvinylchloride; polycarbonate; polyethylene, including PET, HDPE, and LDPE; polytetrafloralethylene; and a combination thereof.

In yet another embodiment of the invention, the container is a resilient, semi-rigid container. In a further aspect, the dispensing opening in the container further comprises a generally curvilinear opening through which a glove is dispensed, the generally curvilinear opening being adapted to allow a first glove to be dispensed and to allow a second glove cuff to at least partially protrude through the opening after separating from the dispensed first glove. In still another aspect, the generally curvilinear dispensing opening is a generally elliptical dispensing opening adapted to partially constrain passage of a glove therethrough. The glove dispenser can be adapted to be at least one of wearable and disposable. In another embodiment of the invention, the dispenser can include a bias disposed between the glove bundle and the case, with the bias urging the glove bundle towards the dispenser opening. In one aspect, the bias is a springably resilient bias. In another aspect, the bias is primarily gravitational.

In one aspect of the dispenser, the attachment device is attached to the dispenser and adapted to make the glove dispenser portable. In another aspect of the dispenser, the attachment device couples with a utility connector on the dispenser, wherein one of a plurality of attachment devices can be interchangeably coupled with the utility connector, and each of the plurality of attachment devices is adapted to removably connect the dispenser to an object.

BRIEF DESCRIPTION OF THE DRAWINGS

These and other features, aspects and advantages of the present invention will be more fully understood when considered with respect to the following detailed description, appended claims and accompanying drawings, wherein:

DESCRIPTION OF THE EMBODIMENTS

The present invention provides a method of folding disposable gloves, and a portable, wearable dispenser adapted to dispense the disposable gloves.

Figure 1:
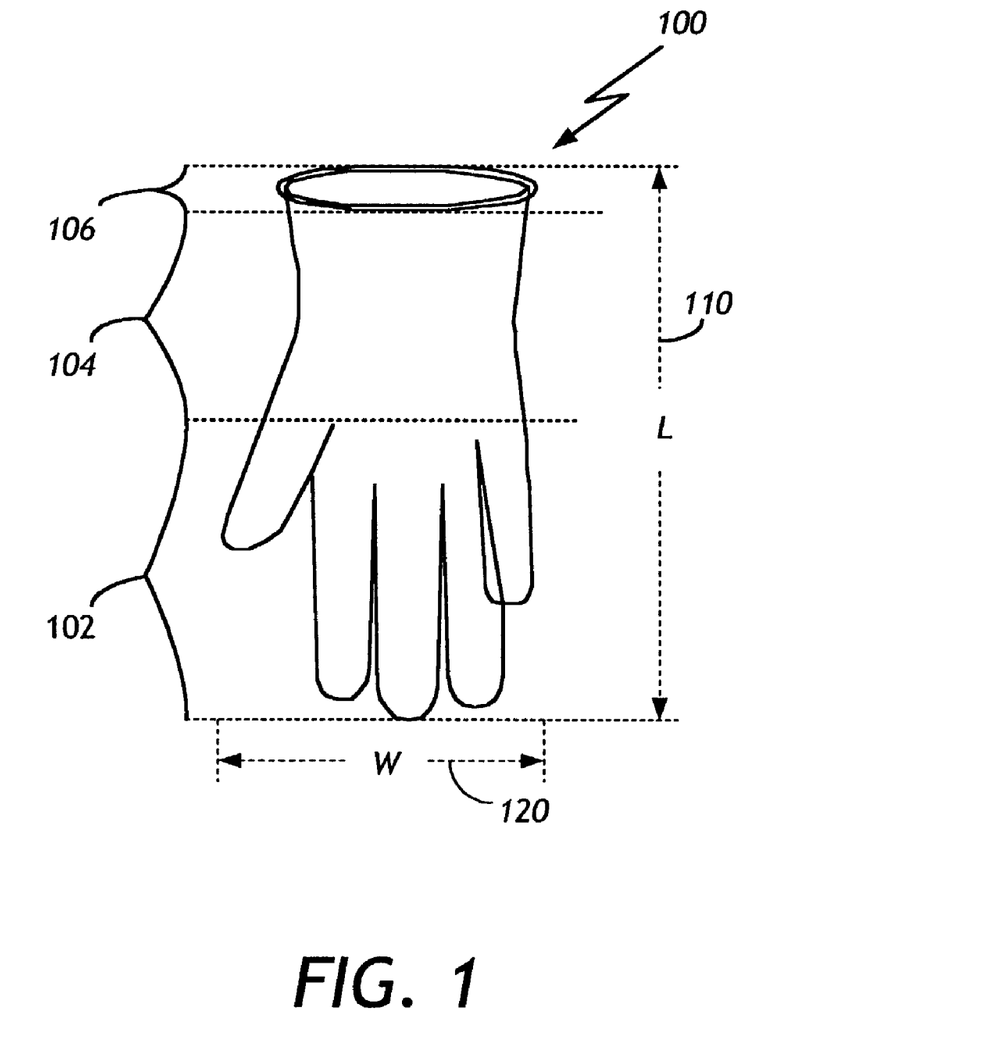
FIG. 1 is an illustration of a glove, defining the relevant portions thereof.

FIG. 1 illustrates glove 100, which can include finger portion 102, hand portion 104, and cuff portion 106. Glove 100 can be a disposable glove and can be made of many materials, for example, latex, nitrile, vinyl/PVC, polyethylene, synthetic, or composite materials. Although glove 100 can be hand-specific, it is desirable that glove 100 be an ambidextrous glove. In addition, cuff portion 106 can be short relative to hand portion 104 or can be a longer, gauntlet-type cuff, whether straight or beaded, rolled or unrolled. Gloves such as glove 100 may be suitable for use in healthcare, law enforcement, and industrial applications, as well as a myriad of consumer activities. Glove 100 can be of a standard length, L, 110, for example, about 200–300 mm (about 7.8"–11.8" inches), and of a standard width, W, 120, for example, about 60–120 mm (about 2.4"–4.8"). Of course, these dimensions are exemplary; skilled artisans would recognize that gloves having other dimensions also could be accommodated by the present invention.

Figure 2A:
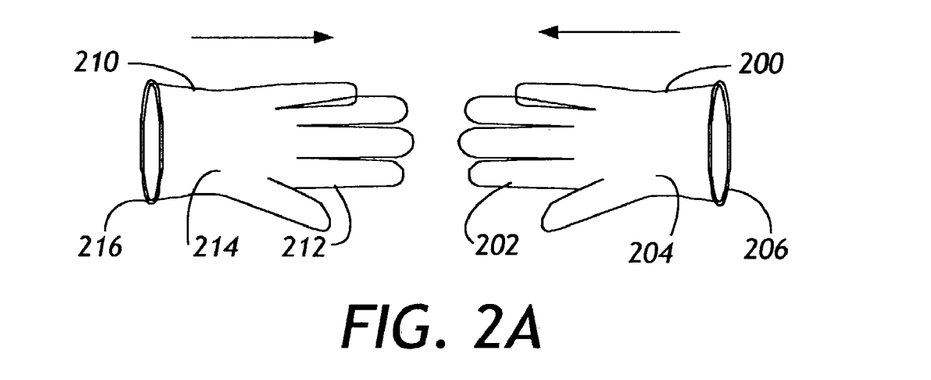
FIGS. 2A–2H are illustrations of a method of folding gloves, according to the present invention.
Figure 2B:
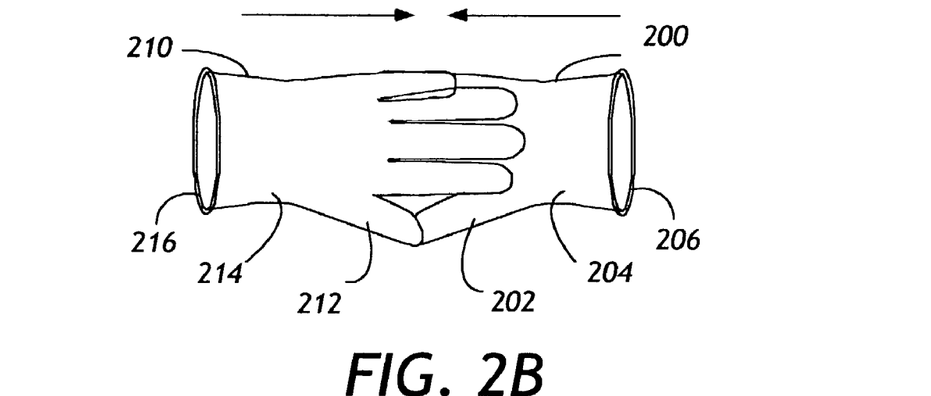
Figure 2C:
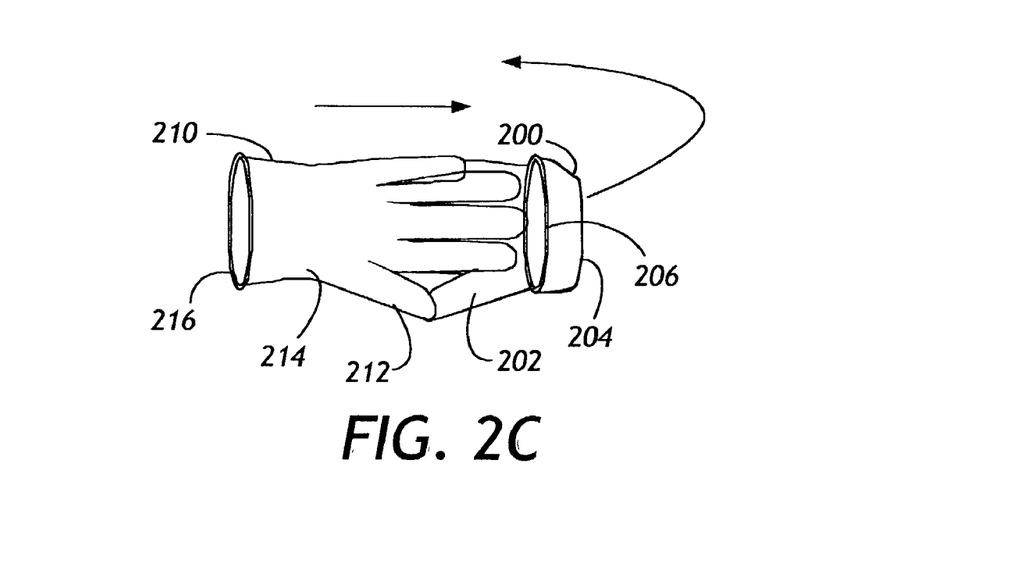
Figure 2D:
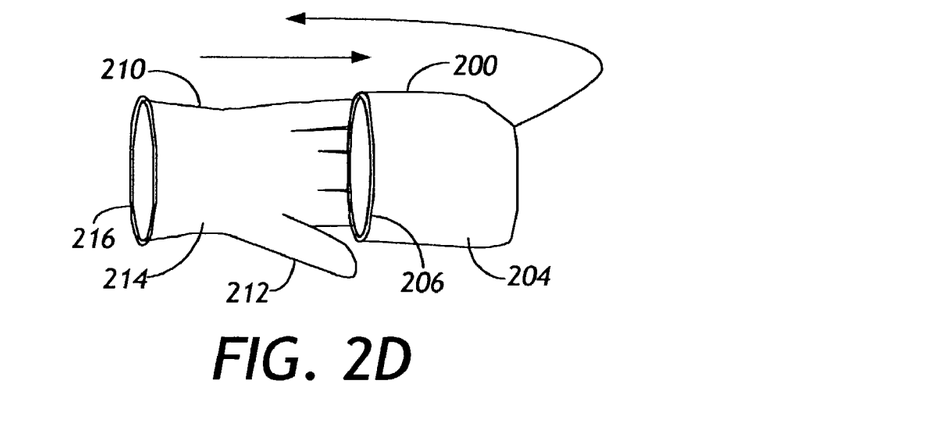
Figure 2E:
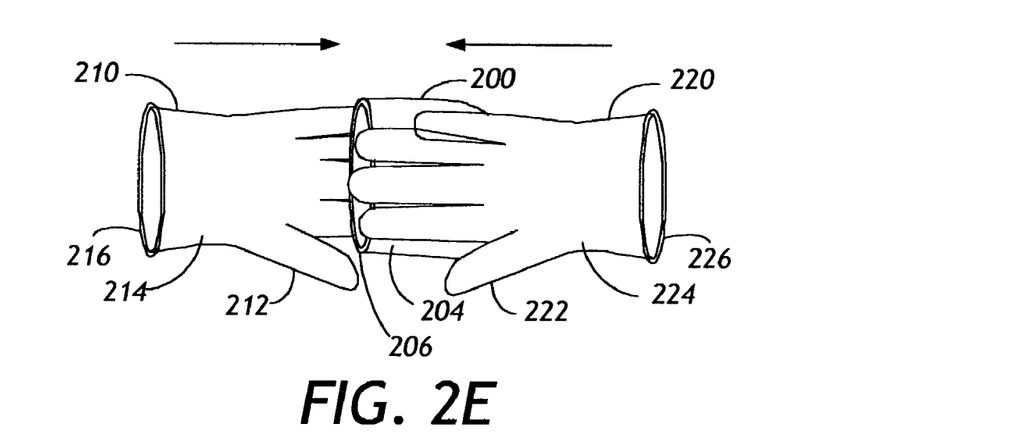
Figure 2F:
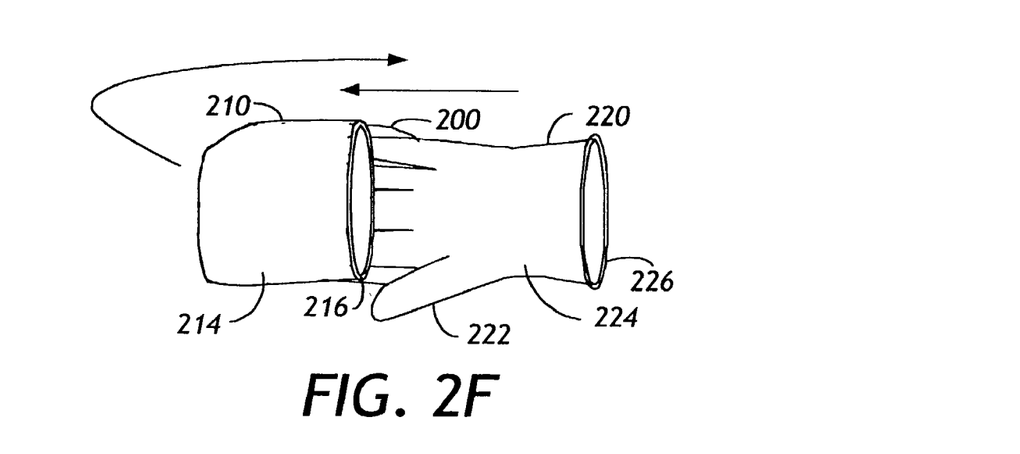
Figure 2G:
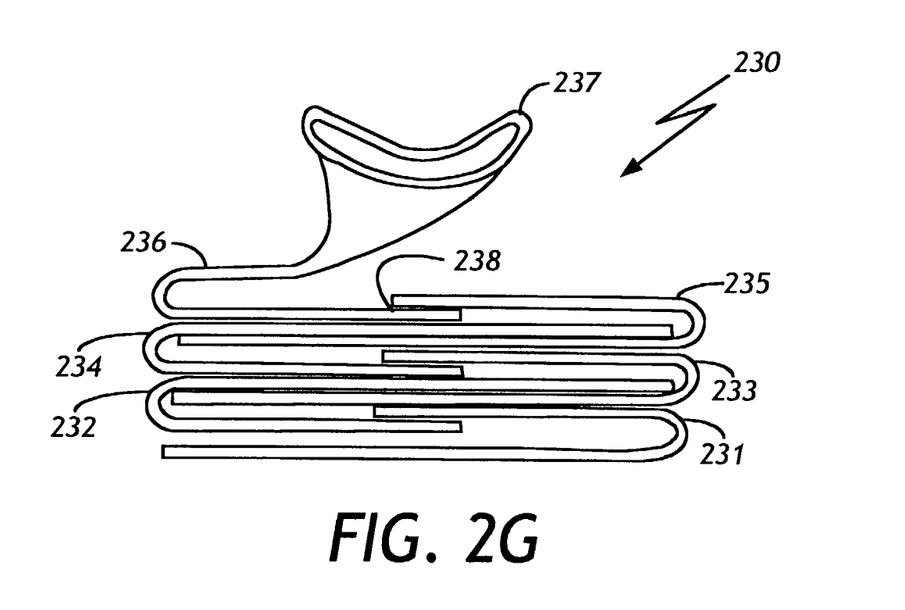
Figure 2H:
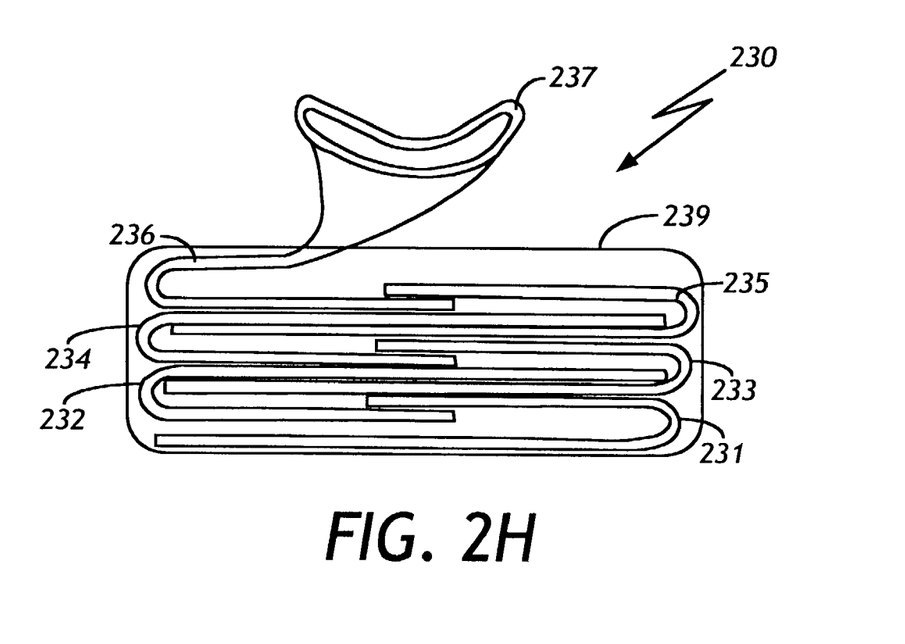
Figure 3:
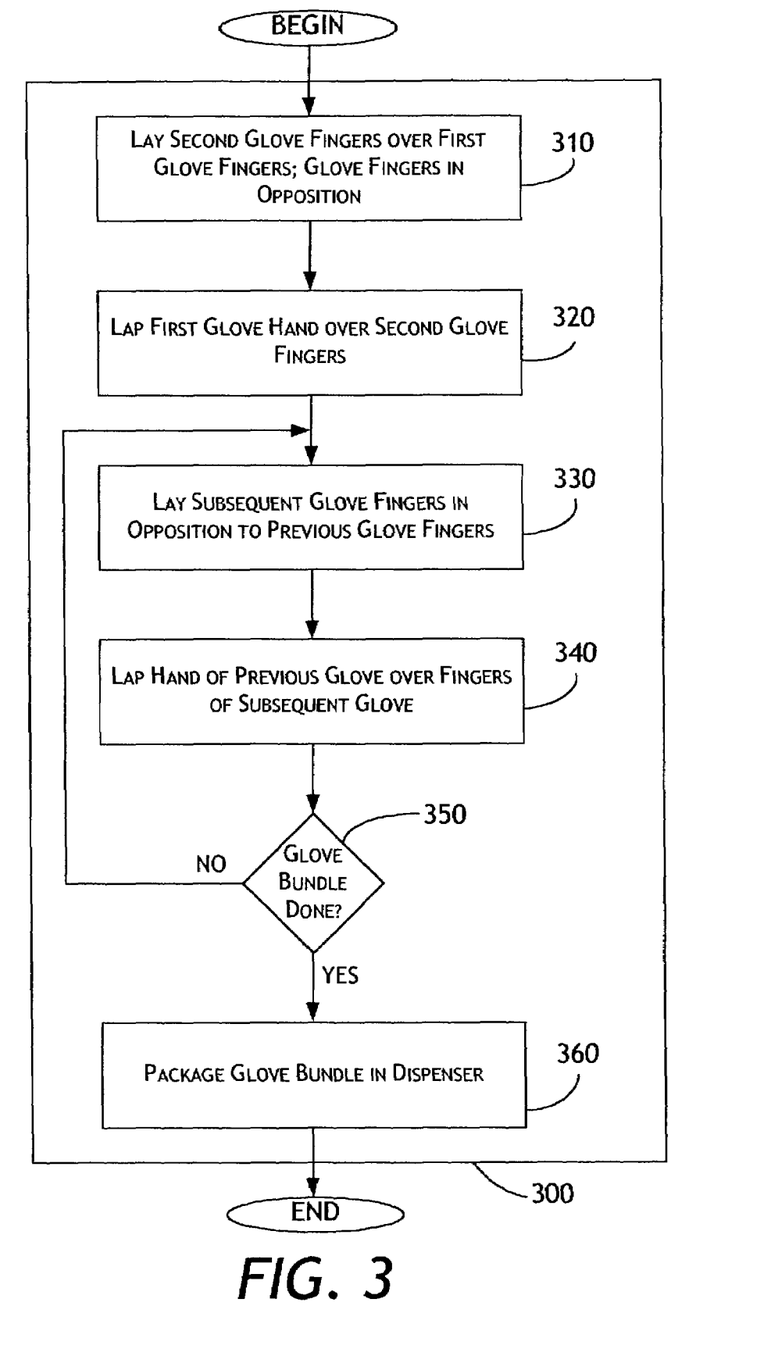
FIG. 3 is a flow diagram summarizing exemplary operations employed in the method depicted in FIGS. 2A–2H.

FIGS. 2A–2H are described concurrently with method 300 in FIG. 3. In one aspect of the invention, illustrated in FIGS. 2A–2H and FIG. 3, an exemplary preselected glove fold can be effected by a lapped superjacent-opposing fold (LSOF) technique or operation. In FIG. 2A, first glove 200 is shown with finger portion 202, hand portion 204, and cuff portion 206. Similarly, second glove 210 is shown with finger portion 212, hand portion 214, and cuff portion 216. As described in operation 310, in FIG. 3, finger portion 212 of second glove 210 is superposed on finger portion 202 of first glove 200.

In general, first glove 200 and second glove 210 are axially-aligned, however, finger portion 202 of glove 200 is generally oriented in opposition to finger portion 212 of second glove 210, such that finger portion 202 is proximate to hand portion 214 and finger portion 212 of glove 210 is proximate to hand portion 204 of first glove 200. Thus, finger portion 202 is arranged in a superjacent-opposing relationship, relative to finger portion 212.

In FIG. 2C, which generally corresponds with the beginning of operation 320 in FIG. 3, cuff portion 206 and hand portion 204 of first glove 200 are lapped over finger portion 212 of second glove 210. FIG. 2D generally shows the relative positions of first glove 200 and second glove 210 at the completion of operation 320 in FIG. 3. Typically, cuff portion 206 of first glove 200 can be proximate to hand portion 214 of second glove 210, and hand portion 204 of first glove 200 is generally superposed oh the fingertips of finger portion 212 of second glove 210. Thus, first glove 200 is considered to be lapped over second glove 210, to provide the lapped superjacent-opposing fold (LSOF). It may be desirable to provide an additional fold between hand portion, and the cuff portion where the gloves having long cuff portions, such as gauntlet-, elbow-, and full-length-type gloves.

As illustrated in FIG. 2E, process 300 continues by superposing finger portion 222 of third glove 220 on lapped cuff portion 206 and hand portion 204 of first glove 200. In general, finger portion 222 of third glove 220 is aligned and oriented in the same manner as the finger portion (not shown) of first glove 200; and axially aligned with, but oriented in opposition to, finger portion 212 of second glove 210.

Operation 340 in FIG. 3 is generally illustrated in FIG. 2F, where cuff portion 216 and hand portion 214 of second glove 210 are lapped and superposed upon finger portion 222 of third glove 220 to provide an LSOF fold relative to second glove 210 and third glove 220. Process 300 generally proceeds as illustrated in FIGS. 2D–2F, that is, by repeatedly using operations 330 and 340 to continue the LSOF operation until a glove bundle having a predetermined number of disposable gloves therein is formed (operation 350).

FIG. 2G illustrates glove bundle 230 formed according to the present inventive method. Gloves 231–236 are folded using an LSOF operation and, after a predetermined number of gloves are so folded together glove bundle 230 is formed. Typically, a completed glove bundle 230 has the cuff portion 237 of the last folded glove 236 at the top of bundle 230. However, glove bundle 230 also may be formed so that the finger portion 238 of the last folded glove 236 is generally at the top of bundle 230.

As shown in FIG. 2H, once glove bundle 230 is formed, it then can be packaged in a suitable dispenser 239, as indicated at operation 360. In one embodiment of the invention shown in FIG. 2H, dispenser 239 can be a jacket adapted to contain glove bundle 230 having a predetermined number of gloves 231–236 folded in a lapped, superjacent-opposing fold format, with jacket 239 having a dispensing opening disposed therethrough. Jacket 239 can be, for example, a thin, flexible, conformal wrap snugly fitting glove bundle 230. However, jacket 239 can be a substantially unitary container of any practical material, including, without limitation, cellulosic, board, plastic, rubber, metal, and composite materials having suitable physical characteristics.

In another embodiment of the invention, jacket 239 can be a primary inner dispensing package that is adapted for use within, and in cooperation with, a secondary, outer dispensing package. Exemplary secondary, outer dispensing packages are described, for example, in conjunction with FIGS. 4A–B, 5A–B, and 6, below, although the dispensers in FIGS. 4A–B, 5A–B, and 6, are not required to have a primary, inner dispensing package, and themselves may constitute the primary dispensing package.

In general, the LSOF technique can accommodate alternative configurations in which gloves 200, 210, 220 are first folded longitudinally to reduce the width (e.g., width W 120 in FIG. 1), for example, before performing a LSOF operation. Width reduction can be accomplished by a simple transverse bifold relative to the longitudinal axis of gloves 200, 210, 220, or by a trifold, a partial fold, a tuck, a pleat, a crimp, or a combination thereof. Folding techniques according to the present invention, such as the LSOF technique, provide a compact glove bundle having a preselected number of gloves folded therein.

In one aspect of the LSOF technique, each glove is removed from the glove bundle one-at-a-time thereby minimizing unneeded contact with other gloves. In addition, each glove so folded generally is removed from the glove bundle in a cuff-first orientation, minimizing unnecessary contact with the clean finger portions of unused gloves. Furthermore, a cuff-first orientation is desirable because it tends to facilitate the application of new gloves. Moreover, folding techniques according to the present invention, such as the LSOF technique, impart an attractive force between successive gloves such that the removal of a glove from the glove bundle is slightly opposed by the physical contact between adjacent gloves. However, finger-first dispensing can also be provided, if desired.

Figure 4A:
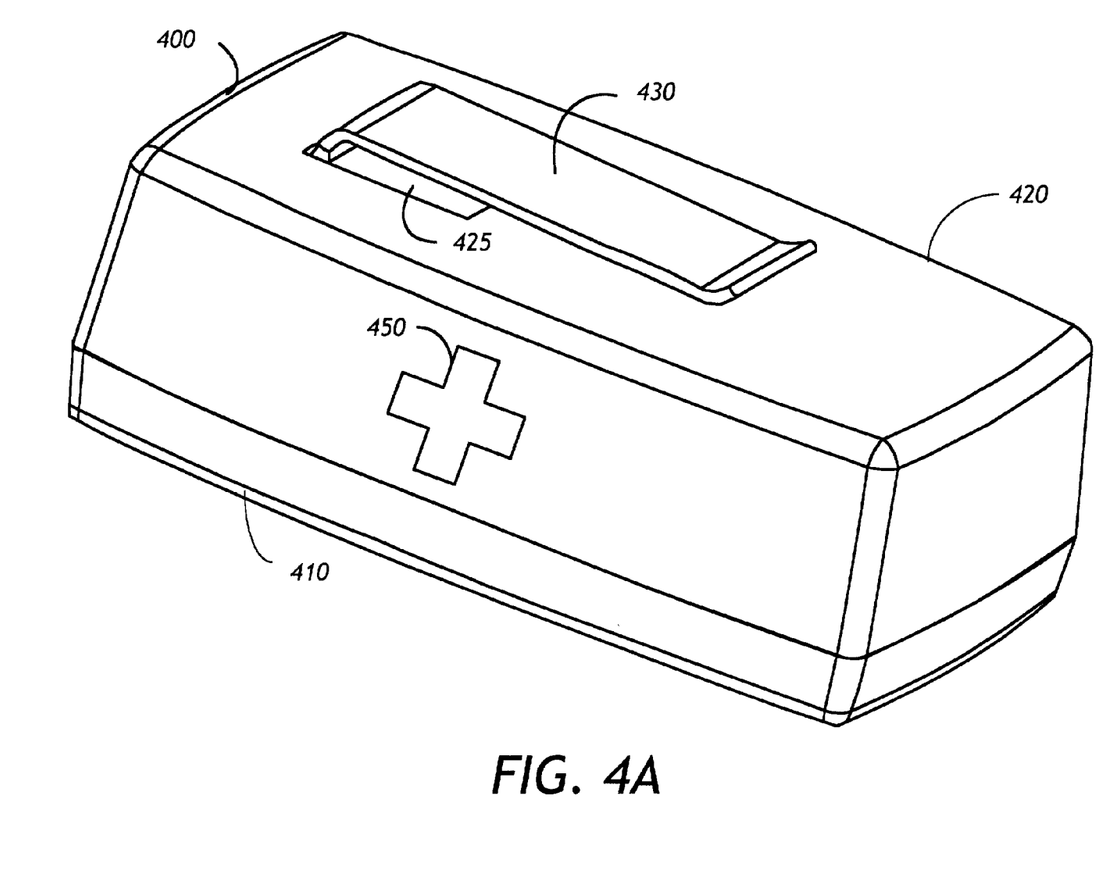
FIG. 4A is an illustration of a bottom perspective view of one aspect of a dispenser according to the present invention.
Figure 4B:
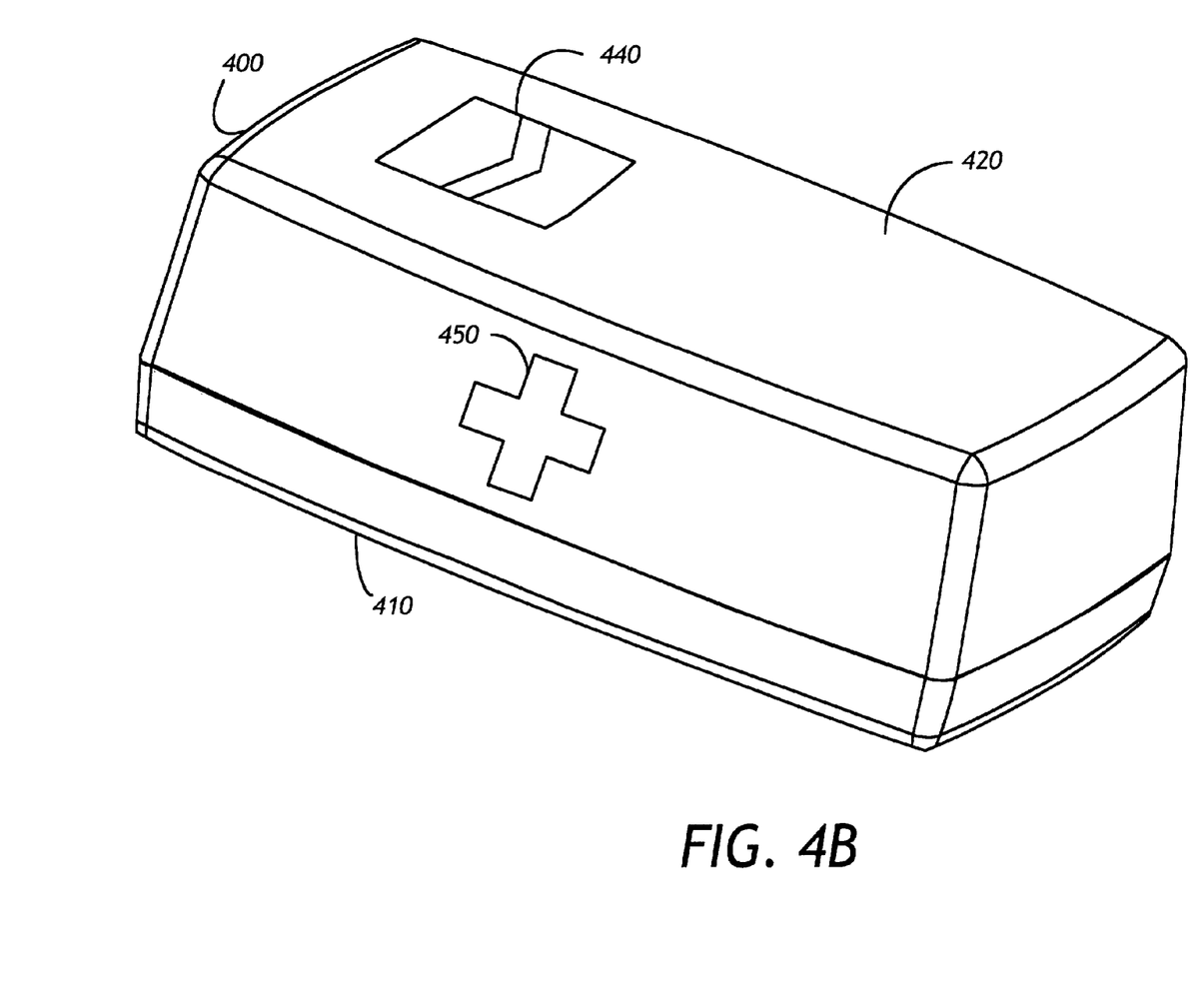
FIG. 4B is an illustration of a bottom perspective view of another aspect of a dispenser according to the present invention.

FIGS. 4A and 4B show bottom perspective views of two respective implementations of dispenser 400, according to the present invention. As illustrated in FIG. 4A, dispenser 400 can include dispenser cap 410, which encloses and is affixed to dispenser case 420. Dispenser cap 410 and case 420 can be formed of the same material or of different, but compatible, materials. Although cap 410 can be removably affixed to case 420, it is desirable that cap 410 be securely fastened to case 420, such that dispenser 400 can be disposable and may not be refilled. Cap 410 can be attached to case 420 by spot tacking which can be implemented by gluing, or heat sealing, selected common points where cap 410 and case 420 meet. Alternatively, cap 410 can be sealably affixed to case 420. By securely fastening and sealing cap 410 to case 420, a reduction in the gross contamination of gloves stored in dispenser 400 can be effected. This feature can be desirable, for example, in health care, emergency, clean room, and food service settings.

Dispenser cap 410, case 420, or both can be a structure composed of suitable natural, synthetic, composite, and laminate materials, including, without limitation, paper and board materials; metals and foils; rubber products; and plastics such as polypropylene; polyvinylchloride; polycarbonate; polyethylene, including PET, HDPE, and LDPE; polytetrafloralethylene; and combinations thereof. Dispenser 400 can be adapted to be an individual, primary glove bundle container in resilient and semi-rigid box form, e.g., as for portable, wearable dispenser, although the container also can be non-rigid, as well.

Furthermore, as described with respect to an embodiment of jacket 239 enwrapping glove bundle 230 in FIG. 2H, dispenser 400 also can be a less-rugged primary inner glove bundle package, such as, for example, a cellulosic or plastic film package formed around the glove bundle, which is adapted for use within, and in cooperation with, a secondary, outer dispensing package. Of course, skilled artisans would recognize that other materials also may be used, including, without limitation, board, plastic (non-film), rubber, metal, and composite materials having suitable physical characteristics. In a "jacket" embodiment, dispenser 400 may have neither a distinct cap nor a distinct case, and the dispensing opening could be disposed at any convenient location of dispenser 400.

In general, it is desirable to provide dispenser 400 dimensioned to snugly hold a complete glove bundle. Dispenser 400 also can be a primary glove bundle container adapted to hold a large-volume glove bundle therein, such as for a countertop holder, under-counter dispenser, and the like, and be of, for example, a cap-and-case or jacket configuration, fabricated of any of the aforementioned exemplary materials. Moreover, dispenser 400 can have indicia 450 disposed thereupon, formed, for example, by embossing, stenciling, etc.

As illustrated in FIG. 4A, attachment device 430 of dispenser 400 can be affixed to base 425, such that dispenser 400 may be removably attached to a clip, a hook, a loop, or other form of attachment apparatus thereby adapting dispenser 400 to be substantially wearable by a glove user, for example, by being attachable to a service belt, article of clothing, rucksack, or duty pack which may be worn by the glove user. Furthermore, attachment device 430 can be movable in one or more directions on base 425 to facilitate the wearable, portable aspects of this invention. In addition, attachment device 430 can be an open of material, a hook-and-loop-type fastener, a double-sided adhesive fastener, a snap, and the like.

In another aspect of dispenser 400, as illustrated in FIG. 4B, bottom surface 420 can be disposed with a utility connector 440, which accepts, and couples with, one of a plurality of attachment devices, each device adapted to be interchangeable with connector 440 and removably connect dispenser 400 to an object such as a person's clothes, duty belt, rucksack, utility bag, vehicle, a counter, and the like.

In one embodiment of the invention, it is desirable that dispenser 400 be provided as a handy, single-use, wearable glove dispenser. The single-use aspect allows dispenser 400 to be properly discarded when the gloves within are exhausted, thereby reducing the occurrence of cross-contamination by reusing glove dispenser 400, for example, in emergent, frontline settings, in which blood and other bodily fluids, waste, and tissue are frequently present.

In another embodiment of the invention, dispenser 400 may be adapted to be re-usable and to receive a sanitary, prepackaged glove bundle having a predetermined number of gloves hygenically disposed therein. In this embodiment, the prepackaged glove bundle can be a primary, inner dispensing package, or jacket, adapted for use within, and in cooperation with, a secondary, outer dispensing package. In one aspect of this embodiment, the aforementioned inner and outer dispensing packages together form the glove dispenser.

Figure 5A:
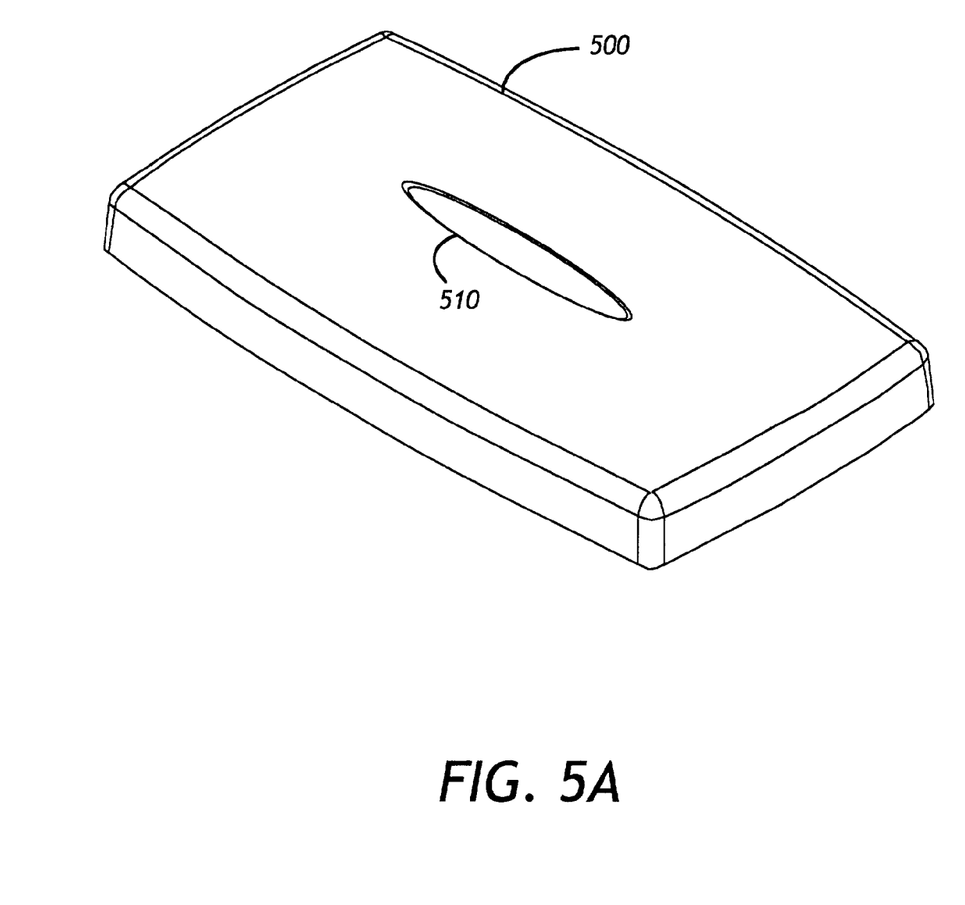
FIG. 5A is an illustration of a top perspective view of one aspect of a dispenser cap according to the present invention.
Figure 5B:
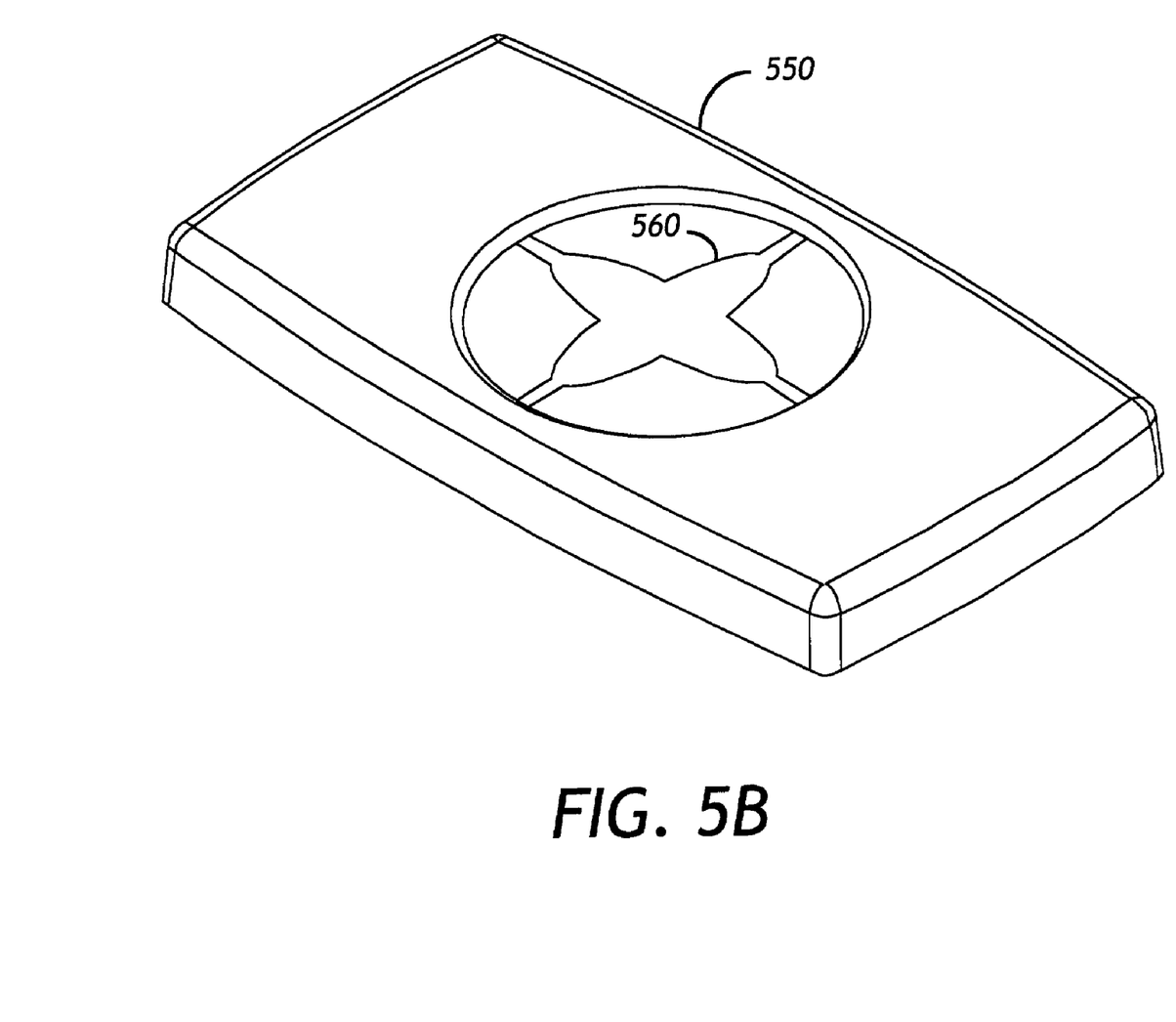
FIG. 5B is an illustration of a top perspective view of one aspect of a dispenser cap according to the present invention.

FIGS. 5A and 5B illustrate alternative aspects of caps 500, 550, which are analogous to cap 410 in FIGS. 4A, 4B. On top surface of dispensers 500, 550 are disposed respective dispensing openings 510, 560. Dispensing openings 510, 560 can be adapted in size and shape to provide a counterforce on the interfolded gloves that are being dispensed, which force acts in cooperation with the attractive force between adjacent LSOF-folded gloves, as described, relative to FIGS. 2A–2F, above. The counterforce provided by opening 510, 560 and the force imparted upon gloves by LSOF operation 300, is such that one glove is dispensed at a time, preferably cuff-first, and subsequent gloves do not bulge or pull-through opening 510, 560. Thus, the forces that restrain the removal of the glove from dispenser are both a counterforce imposed by opening 510, 560, but also the attractive force imparted upon adjacent gloves as a result of being folded by the LSOF operation. These forces are insufficient, however, to unduly encumber glove removal from the dispenser by the glove user, and can be, for example, primarily frictional or stictional, in nature.

In one embodiment of the invention, as illustrated in FIG. 5A, opening 510 is a generally curvilinear opening, such as an ellipse, the aspect ratio of which providing the desirable amount of counterforce. In addition, opening 510 can be generally rectilinear in shape, with the aspect ratio of the rectilinear shape providing the desirable amount of counter force. Typically, opening 510 can be formed at the center of cap 510 however, dispensing opening 510 may be formed on any appropriate side or portion of a dispenser, such a dispenser 400.

In another aspect of the invention, shown in FIG. 5B, opening 560 also is a generally curvilinear opening, but can be, for example, two ellipses oriented generally orthogonally to each other. Opening 560 also can constitute intersecting rectilinear slots. Again, the aspect ratio of the constituent slots can provide the desirable amount of counterforce that assists the inter-glove attractive force in controlling the orderly dispensing of gloves. In this case, opening 560 can provide improved access to the glove bundle.

Figure 6:
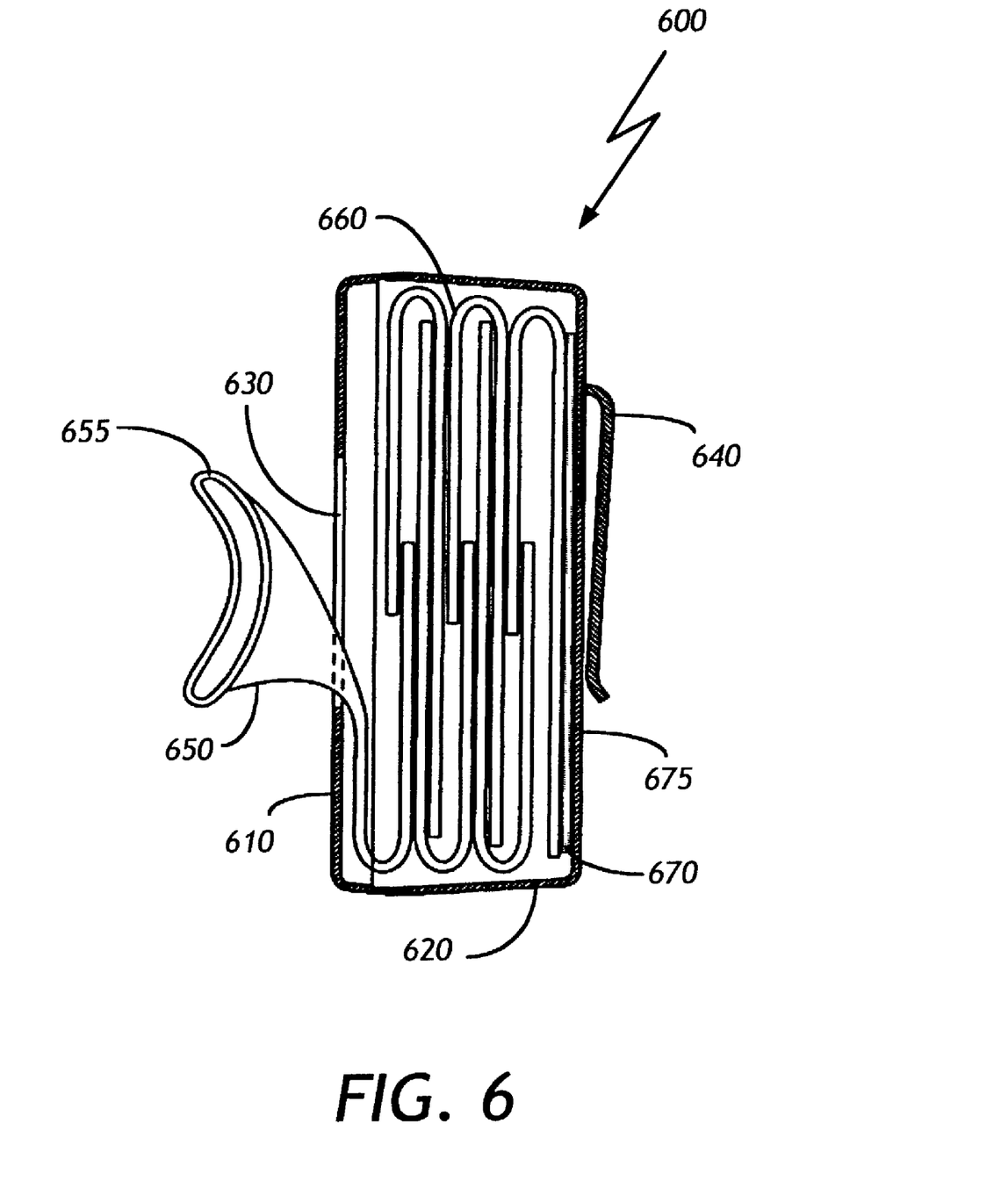
FIG. 6 is a cross-sectional view of the dispenser according to the present invention.

FIG. 6 illustrates a cross-sectional view through exemplary glove dispenser 600 having a glove bundle 660 with a predetermined number of gloves disposed therein. Glove dispenser 600 can include dispenser cap 610, which is adapted to enclose dispenser case 620. Cap 610 can be sealably affixed to case 620, for example, such as by spot tacking with heat or glue, or by completely sealing cap 610 to case 620, such as by overlap sealing with heat or glue. On a surface of dispenser 600, dispensing opening 630 is formed to permit the controlled removal of glove 650.

In general, as in FIGS. 5A and 5B, opening 630 can be formed to provide a counterforce, which can cooperate with an attractive force provided by the interfolded gloves in glove bundle 660, to control the number of gloves which can be removed at one time. When employing a LSOF folding technique as described relative to FIGS. 2A–2F and FIG. 3, each of the gloves 650 in glove bundle 660 can be dispensed cuff-first 655 and one at a time. However, gloves 650 in glove bundle 660 can be disposed to be dispensed fingers-first and, for example, two-at-a-time.

In one aspect of the present invention, each of the gloves 650 in glove bundle 660 can be dispensed without a bias to provide an additional motive force encouraging glove dispensing. However, where such is desirable, bias 670 can be included in dispenser 600, for example, between wall 675 of dispenser 600 and glove bundle 660. Bias 670 can be made of a springably resilient material that is held in compressive tension by glove bundle 660. In addition, bias 670 can be gravitational. Biasing can be desirable, for example, when there are a large number of gloves in glove bundle 660, when the individual gloves 650 tend to be relatively thick, or when the attractive forces between adjacent gloves is relatively high, and so forth. When bias 670 is used, it may be necessary to adjust the configuration of dispensing opening 630 such that the proper counter force in dispensing of glove 650 is provided thereby.

Bias 670 may be desirable where the dimensions of the container may be such that the distance from the top of glove bundle 660 to dispensing opening 630 exceeds, for example, about ⅔ of the glove length, such as L 110 in FIG. 1. Bias 670 can be, for example, a springably-resilient biased piece of cardboard, or a springably-resilient biased spring-and-flat arrangement, juxtaposed between glove bundle 660 and back wall 675 of case 620.

Many alterations and modifications may be made by those having ordinary skill in the art, without departing from the spirit and scope of the invention. Therefore, it must be understood that the illustrated embodiments have been set forth only for the purposes of example, and that it should not be taken as limiting the invention as defined by the following claims. The following claims are, therefore, to be read to include not only the combination of elements which are literally set forth, but all equivalent elements for performing substantially the same function in substantially the same way to obtain substantially the same result. The claims are thus to be understood to include what is specifically illustrated and described above, what is conceptually equivalent, and also what incorporates the ideas of the invention.

What is claimed is:

1. A combination glove dispenser and gloves, comprising:
   a. a glove bundle comprising a predetermined number of gloves, each glove having a finger portion, a hand portion, a cuff portion, a width, and a longitudinal axis, the predetermined number of gloves positioned in a dispenser housing in a folded configuration comprising:
      (1) a second glove being folded along the longitudinal axis to reduce its width, the finger portion of the second glove approximately adjacent the finger portion of a first glove, the first glove being folded along the longitudinal axis to reduce its width, the second glove finger portion being disposed approximately parallel and oriented generally opposite the first glove finger portion, such that the second glove finger portion is in a superjacent opposing relationship relative to the first glove finger portion;
      (2) the cuff portion of the first glove disposed over the finger portion of the second glove, providing a lapped, superjacent opposing fold;
      (3) the finger portion of a third glove, which is folded along the longitudinal axis to reduce its width, superimposed approximately adjacent the finger portion of the second glove, the third glove finger portion being disposed approximately parallel and oriented generally opposite the second glove finger portion such that the third glove finger portion is in a superjacent opposing relationship relative to the second glove finger portion;
      (4) the cuff pardon of the second glove disposed over the finger portion of the third glove, providing a lapped, superjacent opposing fold;
   b. the dispenser housing comprising a first end and a second end adapted to enwrap the glove bundle inrerfoided by lapped, superjacent opposing folds; and
   c. an attachment device in mechanical communication with the dispenser housing comprising a curved portion positioned closer to the first end than the second end of the housing.

2. The combination glove dispenser and gloves of claim 1, wherein each glove is made from at least one of latex, nitrile, vinyl, PVC, and polyethylene.

3. The combination glove dispenser and gloves of claim 1, wherein the dispenser housing comprises a rigid housing comprising an opening.

4. The combination glove dispenser and gloves of claim 1, wherein attachment device is directly coupled to the dispenser housing.

5. A combination glove dispenser and plurality of gloves, comprising:
   a. a case adapted to contain a glove bundle having a predetermined number of gloves folded in a lapped, superjacent-opposing fold format; each glove comprising a finger portion, a hand portion, a cuff portion, a first lengthwise axis, and a second axis perpendicular to the first axis:
      1/ wherein the first glove is folded along the second axis such that the cuff portion of the first glove is folded over the finger portion of a second glove; and
      2/ wherein the second glove is folded along the second axis such that the cuff portion of the second glove is folded over the finger portion of a third glove;
   b. a dispenser housing enwrapping the glove bundle; and
   c. an attachment device in mechanical communication with the dispenser housing, the attachment device being rotatable relative to the housing.

6. The combination glove dispenser and plurality of gloves according to claim 5, wherein the dispenser housing comprises a dispenser opening adapted to cooperate with a tension of the glove bundle to dispense one glove at a time in a cuff-first orientation.

7. The combination glove dispenser and plurality of gloves according to claim 5, wherein the dispenser housing is made from at least one of a board material and a plastic material.

8. The combination glove dispenser and plurality of gloves according to claim 6, further comprising a bias urging the glove bundle towards the dispenser opening.

9. The combination glove dispenser and plurality of gloves according to claim 8, wherein the bias is a springably resilient bias disposed between the glove bundle and the dispenser housing.

10. The combination glove dispenser and plurality of gloves according to claim 9, wherein the bias is gravitational.

11. The combination glove dispenser and plurality of gloves according to claim 5, wherein the attachment device is directly coupled to the dispenser housing.

12. The combination glove dispenser and plurality of gloves according to claim 5, wherein is the dispenser housing is made from a semi-rigid structure.

13. The combination glove dispenser and plurality of gloves according to claim 12, wherein the semi-rigid structure comprises at least one of a polyethylene, including PET, HDPE and LDPE; a polypropylene; a polyvinylchloride; a polycarbonate; a polytetrafloralethylene; and a combination thereof.

14. The combination glove dispenser and plurality of gloves according to claim 6, wherein the dispenser opening further comprises a generally curvilinear opening through which a glove is dispensed, the generally curvilinear opening being adapted to allow a first dispensed glove to be dispensed and to allow a second glove cuff to be dispensed to at least partially protrude through the opening after separating from the first dispensed glove.

15. The combination glove dispenser and plurality of gloves according to claim 5, wherein the glove dispenser is adapted to be at least one of wearable and disposable.

16. The combination glove dispenser and plurality of gloves according to claim 6, wherein the combination dispenser housing and attachment device is configured to be clipped onto an object.

17. The combination glove dispenser and plurality of gloves according to claim 6, wherein the dispenser opening further comprises a generally rectilinear opening through which a glove is dispensed, the generally rectilinear opening being adapted to allow a first dispensed glove to be dispensed and to allow a second glove cuff to be dispensed to at least partially protrude through the opening after separating from the first dispensed glove.

18. The combination glove dispenser and plurality of gloves of claim 5, wherein the dispenser opening further comprises a generally curvilinear opening through which a glove is dispensed, the generally curvilinear opening being adapted to allow a first dispensed glove to be dispensed and to allow a second glove cuff to be dispensed to at least partially protrude through the opening after separating from the first dispensed glove.

19. A combination glove dispenser and gloves, comprising:
   a. a glove bundle disposed in a dispenser housing, the glove bundle comprising a predetermined number of gloves, each glove having a finger portion, a hand portion, a cuff portion, a width, a first axis, and a second axis perpendicular to the first axis, the predetermined number of gloves positioned in a dispenser housing in a folded configuration comprising:
      (1) a first glove folded along the first axis and the second axis such that the finger portion of a second glove is disposed between the cuff portion and the finger portion of the first glove, the second glove also folded along the first axis and the second axis such that the finger portion of a third glove is disposed between the cuff portion and the finger portion of the second glove, the third glove also folded along the first axis and the second axis such that the finger portion of a fourth glove is disposed between the cuff portion and the finger portion of the third glove, the fourth glove also folded along the first axis and the second axis;
   b. a dispenser opening on the housing through which a glove is dispensed, the opening being adapted to allow a first dispensed glove to be dispensed and allow the cuff of a second glove to be dispensed to at least partially protrude through the opening after separating from the first dispensed glove; and
   c. an attachment device mechanically coupled to the dispenser housing, the attachment device being configured for attaching the dispenser housing to a user.

20. The combination glove dispenser and gloves of claim 19, wherein the dispenser housing is made from a rigid material.

21. The combination glove dispenser and gloves of claim 19, wherein the attachment device is directly coupled to the dispenser housing.

22. The combination glove dispenser and gloves of claim 19, wherein the attachment device is rotatable relative to the dispenser housing.

* * * * *